US010583130B2

(12) United States Patent
de Vasconcelos et al.

(10) Patent No.: US 10,583,130 B2
(45) Date of Patent: Mar. 10, 2020

(54) PHARMACEUTICAL FORMULATIONS COMPROMISING NITROCATECHOL DERIVATIVES AND METHODS OF MAKING THEREOF

(71) Applicant: BIAL—Portela & C$^a$, S.A., São Mamede do Coronado (PT)

(72) Inventors: Teofilo Cardoso de Vasconcelos, São Mamede do Coronado (PT); Ricardo Jorge dos Santos Lima, São Mamede do Coronado (PT); Rui Cerdeira de Campos Costa, São Mamede do Coronado (PT)

(73) Assignee: BIAL-PORTELA & CA, S.A., S. Mamede do Coronado (PT)

( * ) Notice: Subject to any disclaimer, the term of this patent is extended or adjusted under 35 U.S.C. 154(b) by 0 days.

(21) Appl. No.: 16/050,602

(22) Filed: Jul. 31, 2018

(65) Prior Publication Data
US 2018/0333402 A1 Nov. 22, 2018

Related U.S. Application Data

(60) Division of application No. 14/825,600, filed on Aug. 13, 2015, now Pat. No. 10,071,085, which is a continuation of application No. 12/750,956, filed on Mar. 31, 2010, now Pat. No. 9,132,094.

(60) Provisional application No. 61/165,778, filed on Apr. 1, 2009.

(51) Int. Cl.
| *A01N 43/40* | (2006.01) |
| *A61K 31/44* | (2006.01) |
| *C07D 413/04* | (2006.01) |
| *C07D 413/14* | (2006.01) |
| *A61K 31/4439* | (2006.01) |
| *A61K 9/16* | (2006.01) |
| *A61K 31/4245* | (2006.01) |
| *A61K 45/06* | (2006.01) |
| *A61K 9/48* | (2006.01) |

(52) U.S. Cl.
CPC ........ *A61K 31/4439* (2013.01); *A61K 9/1611* (2013.01); *A61K 9/1635* (2013.01); *A61K 9/1652* (2013.01); *A61K 9/4808* (2013.01); *A61K 31/4245* (2013.01); *A61K 31/44* (2013.01); *A61K 45/06* (2013.01)

(58) Field of Classification Search
CPC .................................................. A61K 9/4808
USPC ......................................................... 514/340
See application file for complete search history.

(56) References Cited

U.S. PATENT DOCUMENTS

| 1,532,178 A | 4/1925 | Godbold |
| 3,647,809 A | 3/1972 | Reiter et al. |
| 4,065,563 A | 12/1977 | Narayanan et al. |
| 4,264,573 A | 4/1981 | Powell et al. |
| 4,386,668 A | 6/1983 | Parish |
| 4,963,590 A | 10/1990 | Backstrom et al. |
| 5,236,952 A | 8/1993 | Bernauer et al. |
| 5,476,875 A | 12/1995 | Bernauer et al. |
| 5,633,371 A | 5/1997 | Bernauer et al. |
| 5,705,703 A | 1/1998 | Bernauer et al. |
| 5,840,769 A | 11/1998 | Kolter et al. |
| 6,206,110 B1 | 3/2001 | Slaughter, Jr. et al. |
| 6,361,794 B1 | 3/2002 | Kushla et al. |
| 6,500,867 B1 | 12/2002 | Virkki et al. |
| 6,509,363 B2 | 1/2003 | Salituro et al. |
| 6,512,136 B1 | 1/2003 | Benes et al. |
| 6,521,136 B1 | 2/2003 | Sfez et al. |
| 6,627,646 B2 | 9/2003 | Bakale et al. |
| 6,660,753 B2 | 12/2003 | Van Wagenen et al. |
| 7,041,685 B2 | 5/2006 | Cai et al. |
| 7,112,595 B2 | 9/2006 | Wagenen et al. |
| 7,144,876 B2 | 12/2006 | Cai et al. |
| 7,317,029 B2 | 1/2008 | Cai et al. |
| 7,435,750 B2 | 10/2008 | Cai et al. |
| 7,553,964 B2 | 6/2009 | Liu et al. |
| 8,168,793 B2 | 5/2012 | Learmonth et al. |
| 8,524,746 B2 | 9/2013 | Learmonth et al. |
| 8,536,203 B2 | 9/2013 | Learmonth et al. |
| 8,907,099 B2 | 12/2014 | Learmonth et al. |
| 8,975,410 B2 | 3/2015 | Learmonth et al. |
| 9,126,988 B2 | 9/2015 | Russo et al. |
| 2002/0012701 A1 | 1/2002 | Kolter et al. |
| 2003/0055085 A1 | 3/2003 | Wagenen et al. |
| 2004/0097555 A1 | 5/2004 | Ohkawa et al. |
| 2004/0138281 A1 | 7/2004 | Wikstrom et al. |

(Continued)

FOREIGN PATENT DOCUMENTS

| CN | 1173926 A | 5/2001 |
| CN | 1340500 A | 3/2002 |

(Continued)

OTHER PUBLICATIONS

Russian Office Action for copending RU Application No. 2011144145, dated Apr. 6, 2015, with English language translation.
Mexican Office Action for copending MX Application No. 2011-010311, dated Feb. 2, 2016, with English language translation.
International Search Report for PCT/PT2006/000020, dated Oct. 10, 2006.
CMU Pharmaceutical polymorphism, Internet p. 1-3 (2002) printout Apr. 3, 2008.
Singhal et al., "Drug Polymorphism and Dosage Form Design: a Practical Perspective," Advanced Drug Delivery Reviews 56, p. 335-347, (2004).
Walter de Gruyter, Concise Encyclopedia Chemistry, NY, 1993, 872-873.

(Continued)

*Primary Examiner* — Layla Soroush
(74) *Attorney, Agent, or Firm* — McCarter & English, LLP; Steven G. Davis; Wei Song

(57) ABSTRACT

The present disclosure relates to compositions and pharmaceutical formulations comprising at least one active pharmaceutical ingredient chosen from nitrocatechol derivatives of formula I as defined herein and salts, esters, hydrates, solvates and derivatives thereof and methods of making said compositions and pharmaceutical formulations.

24 Claims, No Drawings

(56) References Cited

U.S. PATENT DOCUMENTS

| | | |
|---|---|---|
| 2004/0171645 A1 | 9/2004 | Bartoszyk et al. |
| 2006/0019956 A1 | 1/2006 | Green |
| 2006/0160812 A1 | 7/2006 | Schubert et al. |
| 2006/0173074 A1 | 8/2006 | Ellmen et al. |
| 2006/0257473 A1 | 11/2006 | Puranajoti |
| 2007/0013830 A1 | 1/2007 | Hayakawa |
| 2007/0026054 A1 | 2/2007 | Theobald et al. |
| 2007/0048384 A1 | 3/2007 | Rosenberg et al. |
| 2007/0078133 A1 | 4/2007 | Liu et al. |
| 2007/0117165 A1 | 5/2007 | Presnell et al. |
| 2007/0219187 A1 | 9/2007 | Bessis et al. |
| 2007/0299110 A1 | 12/2007 | Gagliardi et al. |
| 2008/0051441 A1 | 2/2008 | Brown et al. |
| 2008/0071184 A1 | 3/2008 | Carter |
| 2008/0167286 A1 | 7/2008 | Gopalakrishnan et al. |
| 2008/0269236 A1 | 10/2008 | Ji et al. |
| 2009/0000437 A1 | 1/2009 | Johnson et al. |
| 2009/0054437 A1 | 2/2009 | Learmonth et al. |
| 2009/0111778 A1 | 4/2009 | Apodaca et al. |
| 2009/0162283 A1 | 6/2009 | Bando et al. |
| 2009/0227626 A1 | 9/2009 | Deraeve et al. |
| 2009/0312347 A1 | 12/2009 | Dahl et al. |
| 2010/0004284 A1 | 1/2010 | Farina et al. |
| 2010/0112301 A1 | 5/2010 | Powers |
| 2010/0113529 A1 | 5/2010 | Learmonth et al. |
| 2010/0168113 A1 | 7/2010 | Learmonth et al. |
| 2010/0256193 A1 | 10/2010 | Cardoso De Vasconcelos et al. |
| 2010/0256194 A1 | 10/2010 | Cardoso de Vasconcelos et al. |
| 2011/0014282 A1 | 1/2011 | De Vasconcelos |
| 2011/0112301 A1 | 5/2011 | Learmonth et al. |
| 2011/0301204 A1 | 12/2011 | De Almeida et al. |
| 2012/0196904 A1 | 8/2012 | Learmonth et al. |
| 2013/0324578 A1 | 12/2013 | Soares Da Silva et al. |
| 2013/0331416 A1 | 12/2013 | Learmonth et al. |
| 2014/0024682 A1 | 1/2014 | Learmonth et al. |
| 2014/0045900 A1 | 2/2014 | Soares Da Silva et al. |
| 2014/0350057 A1 | 11/2014 | Russo et al. |
| 2015/0072977 A1 | 3/2015 | Learmonth et al. |
| 2015/0166519 A1 | 6/2015 | Learmonth |
| 2015/0359783 A1 | 12/2015 | De Vasconcelos et al. |
| 2016/0009699 A1 | 1/2016 | Learmonth et al. |
| 2016/0009700 A1 | 1/2016 | Russo et al. |

FOREIGN PATENT DOCUMENTS

| | | |
|---|---|---|
| DE | 3740383 A1 | 6/1988 |
| EP | 0237929 B1 | 9/1987 |
| EP | 0372654 A2 | 6/1990 |
| EP | 0487774 A1 | 11/1990 |
| EP | 0462639 A1 | 12/1997 |
| EP | 1167342 A1 | 1/2002 |
| EP | 1845097 A1 | 10/2007 |
| EP | 1881979 A1 | 1/2008 |
| FR | 1260080 A | 5/1961 |
| JP | 10-67651 A | 3/1998 |
| JP | 2002-20319 A | 1/2002 |
| JP | 2003-116966 A | 4/2003 |
| JP | 2007-506797 A | 3/2007 |
| JP | 2008-509195 A | 3/2008 |
| JP | 2008-162955 A | 7/2008 |
| JP | 2012-522764 B2 | 9/2012 |
| WO | 93/13083 A1 | 7/1993 |
| WO | 99/48484 A2 | 9/1999 |
| WO | 2000/037423 A1 | 6/2000 |
| WO | 2001/012627 A1 | 2/2001 |
| WO | 2001/068083 A1 | 9/2001 |
| WO | 2002/017175 A1 | 2/2002 |
| WO | 2002/068417 A2 | 6/2002 |
| WO | 2002/051442 A1 | 7/2002 |
| WO | 2002/060446 A1 | 8/2002 |
| WO | 2002/096867 A2 | 12/2002 |
| WO | 2002/100826 A2 | 12/2002 |
| WO | 2005/013982 A1 | 2/2005 |
| WO | 2005/044797 A1 | 5/2005 |
| WO | 2005/105780 A3 | 11/2005 |
| WO | 2006/061697 A1 | 6/2006 |
| WO | 2006/071184 A1 | 7/2006 |
| WO | 2006/114400 A1 | 11/2006 |
| WO | 2006/129199 A1 | 12/2006 |
| WO | 2006/132914 A1 | 12/2006 |
| WO | 2007/013830 A1 | 2/2007 |
| WO | 2007/113276 A1 | 10/2007 |
| WO | 2007/117165 A1 | 10/2007 |
| WO | 2008/021388 A1 | 2/2008 |
| WO | 2008/094053 A1 | 8/2008 |
| WO | 2008/118331 A2 | 10/2008 |
| WO | 2009/029632 A1 | 3/2009 |
| WO | 2009/116882 A1 | 9/2009 |
| WO | 2010/014025 A1 | 2/2010 |
| WO | 2010/114405 A2 | 10/2010 |
| WO | 2011/107653 A1 | 9/2011 |
| WO | 2012/107708 A1 | 8/2012 |
| WO | 2013/089573 A1 | 6/2013 |

OTHER PUBLICATIONS

Jain et al., "Polymorphism in Pharmacy," Indian Drugs, 1986, 23(6), 315-329.

Muzaffar et al., "Polymorphism and Drug Availability. A Review," J. of Pharmacy (Lahore), 1979, 1(1), 59-66.

U.S. Pharmacopia #23, National Formulary #18, 1995, 1843-1844.

Doelker, english translation of S.T.P. Pratiques (1999), 9(5), 399-409, pp. 1-35.

4th Office Action for Counterpart Mexican Application No. MX/a/2011/010311, dated Dec. 20, 2017.

Canadian Office Action received in connection with Canadian application No. CA 2,757,418, dated Apr. 5, 2017.

European Office Action received in connection with European application No. EP 10714386.9, dated May 19, 2017.

Indian Office Action received in connection with Indian application No. 8315/DELPN/2011, dated Jun. 30, 2017.

Japanese Office Action received in connection with Japanese application No. JP 2015-168153, dated Jun. 26, 2017.

Korean Office Action received in connection with Korean application No. KR 10-2011-7025867, dated Jun. 29, 2017.

Mexican Office Action received in connection with Mexican application No. MX/a/2011/010311, dated May 3, 2017.

English translation of abstract of Japanese Publication No. JP2008-509195, published Mar. 27, 2008.

English translation of abstract of Japanese Publication No. JP2007-506797, published Mar. 22, 2007.

Office Action for counterpart U.S. Appl. No. 12/750,957, dated Nov. 18, 2016.

Office Action for counterpart U.S. Appl. No. 12/750,957, dated Aug. 27, 2015.

Office Action for counterpart U.S. Appl. No. 14/628,630, dated May 12, 2016.

Final Office Action for counterpart U.S. Appl. No. 14/628,630, dated Jan. 27, 2017.

Sun (Particle Size Specifications for Solid Oral Dosage Forms: A Regulatory Perspective, 2010, pp. 1-8).

Office Action for counterpart U.S. Appl. No. 14/541,654, dated Aug. 3, 2015.

Final Office Action for counterpart U.S. Appl. No. 14/541,654, dated Feb. 29, 2016.

Copending U.S. Appl. No. 13/002,287, filed Jul. 29, 2009, to Almeida et al., Titled: Administration Regime for Nitrocatechols.

Copending U.S. Appl. No. 13/442,356, filed Apr. 9, 2012, to Learmonth et al., Titled: Nitrocatechol Derivatives as COMT Inyhibitors.

Copending U.S. Appl. No. 13/583,375, filed Oct. 21, 2011, to Soares de Silva et al., Titled: Administration Regime for Nitrocatechols.

Database Caplus [Online], Chemical Abstracts Service, Columbus, Ohio, US XP002440393, retrieved from STN accession No. 2003:365244, Database accession No. 138:337989, Abstract.

EPO Search Report and Written Opinion for EPO Patent Application No. 06075343, dated Mar. 28, 2006.

Girges et al., "Synthesis of Nicotinoyl Hydrazones, Their N-Oxide Analogs and the Corresponding 3-(5-Aryl-1,3,4-oxadiazol-2-

(56) References Cited

OTHER PUBLICATIONS yl)pyridine Derivatives as Potential Hypoglycemic Agents," Chemical Papers (1992), 46(4), 272-277.
Howse, "Brocesine in Parkinson's disease, Action of a peripheral and central decarboxylase inhibitor in potentiating evodopa," Journal of Neurology, Neurosurgery, and Psychiatry, 36, pp. 27-29 (1973).
International Preliminary Report on Patentability for Int'l Patent Application No. PCT/PT2007/000016, dated Oct. 14, 2008.
International Search Report and Written Opinion for Int'l Patent Application No. PCT/PT2007/000016, dated Jul. 13, 2007.
International Search Report and Written Opinion in PCT/PT2008/000042, dated Apr. 29, 2009.
International Search Report and Written Opinion for Patent Application No. PCT/PT2009/000013, dated Jun. 9, 2009.
International Search Report for Patent Application No. PCT/PT2007/000043, dated Apr. 23, 2008.
International Search Report and Written Opinion for PCT/PT2009/000044, dated Nov. 16, 2009.
International Preliminary Report on Patentability for PCT/PT2009/000044, dated Feb. 10, 2011.
International Preliminary Report on Patentability for PCT/PT2009/000013, dated Sep. 21, 2010.
Korolkovas, A., "Essentials of Medicinal Chemistry," Development of Drugs, Second Ed., pp. 97-103 and 135-137 (1998).
Krogsgaard-Larsen, P. et al., Textbook of Drug Design and Discovery, Third Ed., Table 14.3, pp. 426-427 (2002).
Learmonth, David A. et al., "Chemical Synthesis and Characterization of Conjugates of a Novel Catechol-O-methyltransferase Inhibitor," Bioconjugate Chem., vol. 13, pp. 1112-1118, American Chemical Society (2002).
Morbus Parkinson, Stellenwert von COMT-Hemmem Bestatigt, May 3, 2004, 2 pages.
Nutt, John G. et al., "Pharmacokinetics of Levodopa," Clinical Neuropharmacology, vol. 7, No. 1, pp. 35-49, Raven Press, (1984).
Nutt, John G., "Catechol-O-methyltransferase Inhibitors for Treatment of Parkinson's Disease," Commentary, vol. 351, pp. 1221-1222, the Lancet (Apr. 1998).
Office Action issued in copending U.S. Appl. No. 12/226,260, dated Mar. 20, 2012.
Office Action issued in copending U.S. Appl. No. 12/226,260, dated Nov. 5, 2012.
Office Action issued in copending U.S. Appl. No. 12/524,848, dated Apr. 26, 2012.
Co-pending U.S. Appl. No. 12/226,260, filed May 28, 2009, to Learmonth et al., Titled: New Pharmaceutical Compounds.
Co-pending U.S. Appl. No. 12/524,828, filed Dec. 30, 2009, to Learmonth et al., Titled: Dosage Regimen for COMT Inhibitors.
Co-pending U.S. Appl. No. 12/933,044, filed Sep. 16, 2010, to Learmonth et al., Titled: Crystal Forms of 5-[3-(2,5-Dichloro-4,6-Dimethyl-1-Oxy-Pyridine-3-yl)[1,2,4]Oxadiazol-5-yl]-3-Nitrobenzene-1,2-Diol.
Office Action for counterpart CN Application No. 2016101848763.1, dated Oct. 9, 2017.
Final Office Action for counterpart U.S. Appl. No. 12/750,957, dated Mar. 7, 2018.
Office Action for copending Application No. KR10-2017-7009828, dated Jan. 18, 2018.
Office Action for counterpart CN Application No. 201610250582.8, dated Nov. 23, 2017.
Office Action for counterpart JP Application No. 2015168152, dated Mar. 21, 2017.
Office Action for counterpart Application No. KR1020177009828, dated May 29, 2017.
Office Action for counterpart Application No. IN8411DELNP2011, dated Jul. 31, 2017.
Machine translation of Korean Notice of Final Rejection for Application No. 10-2011-7026011, dated Jan. 10, 2017.
Second Mexican Office Action for counterpart Application No. MX/a/2011/010311, dated Aug. 4, 2016, with English language translation.
Marcoux, Jean-Francois et al., General Preparation of Pyridines and Pyridones via the Annulation of Ketones and Esters, J. Org. Chem., 66, pp. 4194-4199 (2001).
English language translation of JP 2003-116966, dated Apr. 22, 2003.
Non-Final Office Action issued to copending U.S. Appl. No. 12/750,957, dated Oct. 10, 2013.
Final Office Action issued in copending U.S. Appl. No. 12/750,957, dated Jun. 12, 2014.
Australian Office Action for copending AU Patent Application No. 2010231961, dated Apr. 14, 2014.
Australian Office Action for copending AU Patent Application No. 2010231962, dated Apr. 14, 2014.
Japanese Office Action for copending JP Application No. 2012-503350, dated Apr. 23, 2014, with English language translation.
Japanese Office Action for copending JP Application No. 2012-503351, dated Apr. 23, 2014, with English language translation.
Russian Office Action for copending RU Application No. 2011144145, dated Apr. 22, 2014, with English language translation.
Chinese First Office Action for copending CN Application No. 201080022653.X, dated Dec. 3, 2012, with English language translation.
Chinese Second Office Action for copending CN Application No. 201080022653.X, dated Jan. 23, 2014, with English language translation.
International Preliminary Report on Patentability and Written Opinion for PCT/PT2010/000014, dated Oct. 13, 2011.
International Search report and Written Opinion for PCT/PT2010/000015, dated Nov. 23, 2010.
Ivanova, LA, "Technology of Medicinal Forms," Moscow, "Medicina," vol. 2, 1991, pp. 223-224, English translation.
Chinese Third Office Action for copending CN Application No. 201080022653.X, dated Jan. 22, 2015, with English language translation.
Copending U.S. Appl. No. 12/750,956, filed Mar. 31, 2010 to Teofilo Cardoso de Vasconcelos et al., Titled: Pharmaceutical Formulation Comprising Nitrocatechol Derivatives and Methods of Making Thereof.
Office Action issued in copending U.S. Appl. No. 12/750,956, dated Oct. 15, 2012.
Mexican Office Action for copending MX Application No. 2011-010415, dated Aug. 19, 2014, with English language translation.
Office Action issued in copending U.S. Appl. No. 12/750,956, dated Jul. 16, 2013.
Office Action issued in copending U.S. Appl. No. 12/750,956, dated Dec. 22, 2014.
Notice of Allowance for copending U.S. Appl. No. 12/750,956, dated May 13, 2015.
Doelker, english translation of Ann. Pharm. Fr., (2002), 60: 161-176, pp. 1-39.
Taday et al., "Using Terahertz Pulse Spectroscopy to Study the Crystalline Structure of a Drug: a Case Study of the Polymorphs of Ranitidine Hydrochloride," J. of Pharm. Sci., 92(4), (2003), pp. 831-838.
Otsuka et al., "Effect of Polymorphic Forms of Bulk Powders on Pharmaceutical Properties of Carbamazepine Granules," Chem. Pharm. Bull., 47(6), pp. 852-856 (1999).
Advisory Action issued in copending U.S. Appl. No. 12/750,956, dated Dec. 2, 2013.
Communication pursuant to Rules 161(1) and 162 EPC received from the EPO in copending application PCT/PT2010/000014, dated Nov. 25, 2011.
Communication pursuant to Article 94(3) EPC received from the EPO in copending application No. 10 713 3803-1453, dated Jul. 15, 2015.
Examiner's comments for Final Rejection in Office Action for JP 2008-162955 with English language translation.
Mexican Office Action for copending MX Application No. 2011-010415, dated May 12, 2015.

(56) References Cited

OTHER PUBLICATIONS

Russian Office Action for copending RU Application No. 2011144145, dated Nov. 23, 2015, with English language translation.
Communication pursuant to Article 94(3) EPC received from the EPO in copending application No. 10 714 386.9-1460, dated Dec. 17, 2015.
Communication pursuant to Rules 161(1) and 162 EPC received from the EPO in copending application PCT/PT2010/000015, dated Nov. 24, 2011.
Kiss et al., "Discovery of long-acting, peripherally selective inhibitor of a catechol-O-methyltransferase," Journal of Medicinal Chemistry, American Chemical society, US, vol. 53, No. 8, pp. 3396-3411, Apr. 22, 2010.
Rasenack et al., "Micron-size drug particles: common and novel micronization techniques," Pharmaceutical Development and Technology, New York, NY, US, vol. 9, No. 1, pp. 1-13, XP009055393, Jan. 1, 2004.
Dmitriyeva et al., "Features of the reaction of some 2-chloronicotinonitriles with hydroxylamine. Synthesis of 3-(1, 2, 4-oxadiazol-3yl) pyridines and their fragmentation under electron impact," IzvestiyaVysshikh UchehnkyZavedenil, Khimiya I Khimicheskaya Teknologiya, 2005, vol. 48, No. 11, pp. 15-17, CAPLUS Abstract, DN 145:103612.
English language translation of Notice of Preliminary Rejection from the Korean Intellectual Property Office in copending Korean Patent Application No. 10-2011-7026011 dated Mar. 31, 2016.
New Examiner's Report for copending Canadian Patent Application No. 2,757,418, dated Apr. 11, 2016.
Japanese Office Action for copending JP application No. 2012-503351, dated Apr. 25, 2015, with English language translation.
Office Action issued in copending U.S. Appl. No. 12/524,848, dated Oct. 29, 2012.
Office Action issued in copending U.S. Appl. No. 12/524,848, dated Jan. 18, 2013.
Office Action issued in copending U.S. Appl. No. 12/750,957, dated Jan. 7, 2013.
Parashos, Sotirios A. et al., "Frequency, Reasons, and Risk Factors of Entacopone Discontinuation in Parkinson Disease," Clin Neuropharmacol, vol. 27, No. 3, pp. 119-123 (Jun. 2004).
Pedrosa, R. et al., "Oxidative and non-oxidative mechanisms of neuronal cell death and apoptosis by L-3,4-dihydroxyphenylalanine (L-DOPA) and dopamine," British Journal of Pharmacology, vol. 137, pp. 1305-1313 (2002).
Poulain, R.F. et al., "Parallel Synthesis of 1,2,4-oxadiazoles from carboxylic acids using an improved uranium-based, activation," Tetrahedron Letters, 42:1495-1498 (2001).
Reches, A. et al., "3-O-Methyldopa inhibits rotations induced by levodopa in rats after unilateral destruction of the nigrostriatal pathway," Official Journal of the American Academy of Neurology, vol. 32, No. 8, pp. 887-888, Neurology, (Aug. 1982).
Smith, Kirsten S. et al., "In vitro Metabolism of Tolcapone to Reactive Intermediates: Relevance to Tolcapone Liver Toxicity," Chem. Res. Toxicol., vol. 16, pp. 123-128, American Chemical Society, (2003).
Soares de Silva, P. et al., "The O-methylated derivative of L-DOPA, 3-O-methyl-L-DOPA, fails to inhibit neuronal and non-neuronal aromatic L-amino acid decarboxylase," Brain Research, vol. 863, pp. 293-297 (2000).
Tervo, Anu J. et al., "A structure-activity relationship study of catechol-O-methyltransferase inhibitors combining molecular docking and 3D QSAR methods," Journal of Computer-Aided Molecular Design, vol. 17, pp. 797-810 (2003).
Tohgi, H. et al., "The significance of 3-O-methyldopa concentration in the cerebrospinal fluid in the pathogenesis of wearing-off phenomenon in Parkinson's disease," Neuroscience Letters, vol. 132, pp. 19-22, (1991).
Vieira-Coelho, M.A. et al., "Effects of tolcapone upon soluble and membrane-bound brain and liver catechol-O-methyltransferase," Brain Research, vol. 821, pp. 69-78 (1999).
Ansel et al., (Ansel's Pharmaceutical Dosage Forms and Drug Delivery systems, 6th edition 1995).
Kristensen et al., "Granulation: A Review on Pharmaceutical Wet-Granulation," Drug Development and Industrial Pharmacy, 13(4 &5), 803-872 (1987).
Copending application PCT/PT2010/000014, filed Mar. 31, 2010 to Bial-Portela & CA, S.A., Titled: Pharmaceutical Formulation Comprising Nitrocatechol Derivatives and Methods of Making Thereof.
Copending application PCT/PT2010/000015, filed Mar. 31, 2010 to Bial-Portela & CA, S.A., Titled: Pharmaceutical Formulation Comprising Nitrocatechol Derivatives and Methods of Making the Same.
Copending U.S. Appl. No. 12/750,957, filed Mar. 31, 2010 to Teofilo Cardoso de Vasconcelos et al., Titled: Pharmaceutical Formulation Comprising Nitrocatechol Derivatives and Methods of making the Same.
International Search Report in copending application PCT/PT2010/000014 dated Jun. 22, 2010.
Written Opinion of the International Searching Authority in copending application PCT/PT2010/000014 dated Jun. 22, 2010.
Al-Mousawi, S.M. et al., "Alkylazinylcarbonitriles as building blocks in heterocyclic synthesis: a route for the synthesis of 4-methyl-2-oxopyridines," Pharmazie, 54, 8, pp. 571-574 (1999).
Al-Omran, F. et al., "Heterocyclic Synthesis via Enaminones: Novel Synthesis of (1H)-Pyridin-2-one, Pyrazolo [1-5-α] pyrimidine and Isoxazole Derivatives Incorporating a N-Methylphthalimide and Their Biological Evaluation," J. Heterocyclic Chem., 42, pp. 307-312 (2005).
Bondvalli et al., "An Efficient Synthesis of Functionalized 2-Pyridones by Direct Route or via Amide/Enolate Ammonium Salt Intermediates," Synthesis, No. 7, pp. 1169-1174 (1999).
Davies, Ian W. et al., "A General [3 α 2 α 1] Annulation Strategy for the Preparation of Pyridine N-Oxides," Organic Letters, vol. 3, No. 2, pp. 209-211 (2001).
English Translation of Chinese Second Office Action for Application No. 201610260582.8, dated Sep. 18, 2017.
Office Action for Russian Application No. 2016152167, dated Mar. 15, 2019 with translation.
Office Action for Chinese Application No. 201610184873.1, dated May 17, 2019 with translation.
Office Action for European Application No. 10714386.9-1114, dated Feb. 8, 2019.
Third Office Action for counterpart Chinese Application No. 201610250582.8, dated Feb. 3, 2019, with translation.
Office Action for counterpart Canadian Application No. 2,757,481, dated Nov. 14, 2018.
English Translation of Office Action for counterpart Korean Application No. 10-2018-7024054, dated Oct. 10, 2018.
Canadian Office Action received in connection with Canadian Application No. CA 2,757,418, dated Sep. 19, 2019.

PHARMACEUTICAL FORMULATIONS COMPROMISING NITROCATECHOL DERIVATIVES AND METHODS OF MAKING THEREOF

CROSS REFERENCE TO RELATED APPLICATIONS

This is a divisional of U.S. patent application Ser. No. 14/825,600, filed Aug. 13, 2015, which was a continuation of U.S. patent application Ser. No. 12/750,956, filed Mar. 31, 2010, and claims the benefit of U.S. Provisional Application No. 61/165,778, filed Apr. 1, 2009, all of which are incorporated herein in their entireties.

FIELD OF THE DISCLOSURE

The present disclosure relates to compositions and pharmaceutical formulations comprising at least one active pharmaceutical ingredient chosen from nitrocatechol derivatives and salts thereof.

BACKGROUND

Levodopa (L-DOPA) has been used in clinical practice for several decades in the symptomatic treatment of various conditions, including Parkinson's disease. L-DOPA is able to cross the blood-brain barrier, where it is then converted to dopamine and increases the levels thereof. However, conversion of L-DOPA to dopamine may also occur in the peripheral tissue, possibly causing adverse effects upon administration of L-DOPA. Therefore, it has become standard clinical practice to co-administer a peripheral amino acid decarboxylase (AADC) inhibitor, such as carbidopa or benserazide, which prevents conversion to dopamine in peripheral tissue.

This has led to an interest in the development of inhibitors of the enzyme catechol-O-methyltransferase (COMT) based on the hypothesis that inhibition of the enzyme may provide clinical improvements in patients afflicted with Parkinson's disease undergoing treatment with L-DOPA, since COMT catalyses the degradation of L-DOPA.

It has been found, as set forth in International Publication Nos. WO 2007/013830 and WO 2007/117165, which are incorporated herein by reference, that compounds of formula I disclosed herein, which are nitrocatechol derivatives, are potent and long-acting COMT inhibitors. Those compounds are both bioactive and bioavailable. Thus, compounds of formula I have potentially valuable pharmaceutical properties in the treatment of some central and peripheral nervous system disorders where inhibition of O-methylation of catecholamines may be of therapeutic benefit, such as, for example, mood disorders; movement disorders, such as Parkinson's disease, parkinsonian disorders and restless legs syndrome; gastrointestinal disturbances; edema formation states; and hypertension. Furthermore, these compounds may also have activity in treating other diseases and disorders, not related to the inhibition of O-methylation of catecholamines.

It has also been found, however, that the compounds of formula I may exhibit a low bulk density, poor solubility and/or poor flow characteristics, which increases the difficulty in formulating and/or manufacturing a dosage formulation containing the active compound.

The inventors have now discovered compositions and formulations thereof comprising at least one active pharmaceutical ingredient ("API") chosen from nitrocatechol derivatives of formula I as defined herein and salts, esters, hydrates, solvates and other derivatives thereof. In various embodiments, the at least one nitrocatechol derivative is 2,5-dichloro-3-(5-(3,4-dihydroxy-5-nitrophenyl)-1,2,4-oxadiazol-3-yl)-4,6-dimethylpyridine 1-oxide or 5-[3-(2,5-dichloro-4,6-dimethylpyridin-3-yl)-[1,2,4]oxadiazol-5-yl]-3-nitrobenzene-1,2-diol. The at least one nitrocatechol derivative may also be a mixture of 2,5-dichloro-3-(5-(3,4-dihydroxy-5-nitrophenyl)-1,2,4-oxadiazol-3-yl)-4,6-dimethylpyridine 1-oxide and 5-[3-(2,5-dichloro-4,6-dimethylpyridin-3-yl)-[1,2,4]oxadiazol-5-yl]-3-nitrobenzene-1,2-diol. In at least one embodiment, the API may be present in granular form. In some embodiments, the compositions and/or formulations may comprise a further API, for example the compositions and/or formulations may comprise, in addition to the at least one API chosen from nitrocatechol derivatives of formula I, further APIs such as L-DOPA, a peripheral amino acid decarboxylase (AADC) inhibitor, such as carbidopa or benserazide.

In further embodiments, the compositions and/or formulations may also comprise at least one phosphate derivative and at least one polyvinylpyrrolidone (PVP) derivative compound. In various exemplary embodiments when the API is granular, the at least one phosphate derivative and at least one PVP derivative compound may, independently, be intragranular (i.e., granulated with the API and/or contained within the same granules as the API), extragranular (i.e., present outside the granules of API), or part intragranular and part extragranular. In yet further embodiments of the present disclosure, the compositions may exhibit a bulk density that is greater than that of the API alone, and that may, in certain embodiments, be significantly increased. In yet further embodiments, the compositions may exhibit good flowability, that may, in certain embodiments, be significantly improved over that of the API alone. The compositions may also exhibit improvements in other characteristics such as compressibility and content uniformity (i.e., the API is homogenously distributed throughout the composition, for example throughout the granule). Use of the methods described herein may also result in improvements in the granule properties of the compositions such as improved granule size and uniformity of granule size and/or of granule mass.

SUMMARY

In accordance with the detailed description and various exemplary embodiments described herein, the present disclosure relates to compositions and formulations thereof comprising at least one API chosen from nitrocatechol derivatives of formula I as defined herein and salts, esters, hydrates, solvates and other derivatives thereof thereof. In various exemplary embodiments, the at least one nitrocatechol derivative may be 2,5-dichloro-3-(5-(3,4-dihydroxy-5-nitrophenyl)-1,2,4-oxadiazol-3-yl)-4,6-dimethylpyridine 1-oxide or 5-[3-(2,5-dichloro-4,6-dimethylpyridin-3-yl)-[1,2,4]oxadiazol-5-yl]-3-nitrobenzene-1,2-diol. The at least one nitrocatechol derivative may also be a mixture of 2,5-dichloro-3-(5-(3,4-dihydroxy-5-nitrophenyl)-1,2,4-oxadiazol-3-yl)-4,6-dimethylpyridine 1-oxide and 5-[3-(2,5-dichloro-4,6-dimethylpyridin-3-yl)-[1,2,4]oxadiazol-5-yl]-3-nitrobenzene-1,2-diol. In at least one embodiment, the API may be present in granular form. In some embodiments, the compositions and/or formulations may comprise a further API, for example the compositions and/or formulations may comprise, in addition to the at least one API chosen from nitrocatechol derivatives of formula I, further APIs such as L-DOPA, a peripheral amino acid decarboxylase (AADC) inhibitor, such as carbidopa or benserazide.

In further embodiments, the compositions and/or formulations may also comprise at least one phosphate derivative and at least one PVP derivative compound. In various exemplary embodiments when the API is granular, the at least one phosphate derivative and the at least one PVP derivative compound may, independently, be intragranular, extragranular, or part intragranular and part extragranular. In yet further embodiments of the present disclosure, the compositions may exhibit a bulk density that is greater than that of the API alone, and that may, in certain embodiments, be significantly increased. In yet further embodiments, the compositions may exhibit good flowability, that may, in certain embodiments, be significantly improved over that of the API alone.

The compositions may also exhibit improvements in other characteristics such as compressibility and content uniformity (i.e., the API is homogenously distributed throughout the composition, for example throughout the granule). Use of the methods described herein may also result in improvements in the granule properties of the compositions such as improved granule size and uniformity of granule size and/or of granule mass.

DETAILED DESCRIPTION

It is to be understood that both the foregoing general description and the following detailed description are exemplary and explanatory only, and are not restrictive of the invention as claimed. Other embodiments of the disclosure will be apparent to those skilled in the art from consideration of the specification and practice of the invention disclosed herein.

In various exemplary embodiments, the present disclosure relates to compositions and formulations thereof comprising at least one API chosen from nitrocatechol derivatives of formula I as defined herein and salts, esters, hydrates, solvates and other derivatives thereof, at least one phosphate derivative, and at least one PVP derivative compound. In at least one embodiment, the API may be present in granular form.

As used herein, the terms "granules," "granular form," "API granules" and variations thereof, are intended to include the particles produced by wet or dry granulation of the API chosen from nitrocatechol derivatives of formula I as defined herein and salts, esters, hydrates, solvates and other derivatives thereof. In various embodiments of the present disclosure, the granules may further comprise at least one phosphate derivative and/or at least one PVP derivative compound.

As used herein, the term "composition," and variations thereof, is intended to mean a composite comprising the at least one API, at least one phosphate derivative, and at least one PVP derivative compound. In certain embodiments, the composition may comprise two or more nitrocatechol derivatives of formula I (i.e. APIs), for example the composition may comprise 2,5-dichloro-3-(5-(3,4-dihydroxy-5-nitrophenyl)-1,2,4-oxadiazol-3-yl)-4,6-dimethylpyridine 1-oxide and 5-[3-(2,5-dichloro-4,6-dimethylpyridin-3-yl)-[1,2,4]oxadiazol-5-yl]-3-nitrobenzene-1,2-diol, at least one phosphate derivative, and at least one PVP derivative compound. In at least one embodiment, the composition may comprise granules of the at least one API, and the at least one phosphate derivative and the at least one PVP derivative compound may, in various embodiments, be independently intragranular (i.e., granulated with the API and/or contained within the same granules as the API), extragranular (i.e., present outside the granules of API), or part intragranular and part extragranular. For example, the phosphate derivative may be 10 wt % to 90 wt %, 20 wt % to 80 wt %, 30 wt % to 70 wt %, 40 wt % to 60 wt %, or about 50 wt % intragranular, with the remaining portion being extragranular. The PVP derivative may be 10 wt % to 90 wt %, 20 wt % to 80 wt %, 30 wt % to 70 wt %, 40 wt % to 60 wt %, or about 50 wt % intragranular, with the remaining portion being extragranular. In various exemplary embodiments, the composition may comprise at least one excipient, and in a further embodiment, the composition may be appropriate for filling a capsule and/or making a tablet, and/or directly administering to patients, for examples packaged as sachets.

As used herein, the terms "formulation," "pharmaceutical formulation," and variations thereof, are intended to include compositions described herein that are further processed or formulated into a dosage form. By way of example only, in various exemplary embodiments, the formulations may comprise a composition described herein, typically in the form of granules, in a dosage form suitable for administration to a subject, such as a capsule or a compressed form such as a tablet. In a further exemplary embodiment, the formulations may comprise a composition described herein, typically in the form of granules, mixed with at least one excipient in a dosage form suitable for administration to a subject, such as a capsule or a compressed form such as a tablet.

As used herein, the nitrocatechol derivatives of formula I are defined as follows:

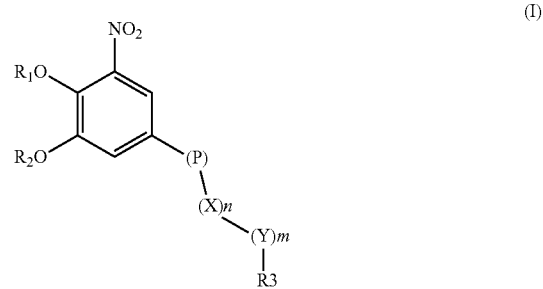

(I)

wherein:
R$_1$ and R$_2$ are independently selected from hydrogen or a group which is hydrolysable under physiological conditions, optionally substituted lower alkanoyl or aroyl;
X is a methylene group;
Y is an atom of oxygen, nitrogen, or sulphur,
n is selected from 0, 1, 2, and 3;
m is 0 or 1;
R$_3$ is a pyridine group chosen from the formulas A, B, C, D, E and F which is connected as indicated by the unmarked bond:

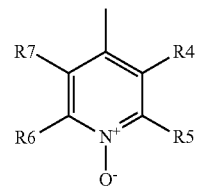

A

-continued

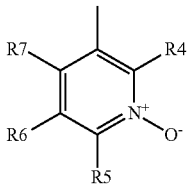

B

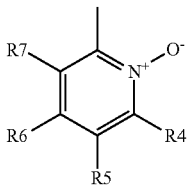

C

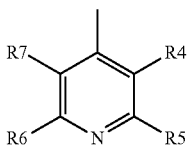

D

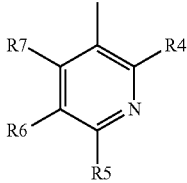

E

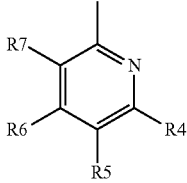

F wherein:
R₄, R₅, R₆, and R₇ are independently chosen from hydrogen, $C_1$-$C_6$-alkyl, $C_1$-$C_6$-thioalkyl, $C_1$-$C_6$-alkoxy, $C_6$-$C_{12}$-aryloxy or a $C_6$-$C_{12}$-thioaryl group, $C_1$-$C_6$-alkanoyl or $C_7$-$C_{13}$-aroyl group, amino, $C_1$-$C_6$-alkylamino, $C_1$-$C_6$-dialkylamino, $C_3$-$C_{12}$-cycloalkylamino, $C_3$-$C_{12}$-heterocycloalkylamino, $C_1$-$C_6$-alkylsulphonyl, $C_6$-$C_{12}$-arylsulphonyl, halogen, $C_1$-$C_6$-haloalkyl, e.g., trifluoromethyl, cyano, nitro or a heteroaryl group; or two or more of residues R₄, R₅, R₆ and R₇ taken together represent aliphatic or heteroaliphatic rings or aromatic or heteroaromatic rings; and
P is a central unit, for example a planar unit, such as those selected from the regioisomers of 1,3,4-oxadiazol-2,5-diyl; 1,2,4-oxadiazol-3,5-diyl; 4-methyl-4H-1,2,4-triazol-3,5-diyl; 1,3,5-triazin-2,4-diyl; 1,2,4-triazin-3,5-diyl; 2H-tetrazol-2,5-diyl; 1,2,3-thiadiazol-4,5-diyl; 1-alkyl-3-(alkoxycarbonyl)-1H-pyrrol-2,5-diyl wherein alkyl is represented by methyl, ethyl, n-propyl and n-butyl and wherein alkoxy is represented by methoxy, ethoxy, n-propoxy and isopropoxy; 1-alkyl-1H-pyrrol-2,5-diyl wherein alkyl is represented by methyl, ethyl, n-propyl and n-butyl; thiazol-2,4-diyl; 1-H-pyrazol-1,5-diyl; pyrimidin-2,4-diyl; oxazol-2,4-diyl; carbonyl; 1H-imidazol-1,5-diyl; isoxazol-3,5-diyl; furan-2,4-diyl; 3-alkoxycarbonylfuran-2,4-diyl wherein alkoxy is represented by methoxy, ethoxy, n-propoxy, and isopropoxy; benzene-1,3-diyl; and (Z)-1-cyanoethen-1,2-diyl. Suitable groups which are hydrolysable under physiological conditions are well known in the art and include groups that form, with the O atom, an ether, ester, or carbonic acid ester linkage.

In one exemplary embodiment, P is chosen from 1,3,4-oxadiazol-2,5-diyl and 1,2,4-oxadiazol-3,5-diyl.

In a further exemplary embodiment, the at least one nitrocatechol derivative of formula I is 2,5-dichloro-3-(5-(3,4-dihydroxy-5-nitrophenyl)-1,2,4-oxadiazol-3-yl)-4,6-dimethylpyridine 1-oxide or 5-[3-(2,5-dichloro-4,6-dimethylpyridin-3-yl)-[1,2,4]oxadiazol-5-yl]-3-nitrobenzene-1,2-diol. The at least one nitrocatechol derivative of formula I may also be a mixture of 2,5-dichloro-3-(5-(3,4-dihydroxy-5-nitrophenyl)-1,2,4-oxadiazol-3-yl)-4,6-dimethylpyridine 1-oxide and 5-[3-(2,5-dichloro-4,6-dimethylpyridin-3-yl)-[1,2,4]oxadiazol-5-yl]-3-nitrobenzene-1,2-diol. In embodiments where the at least one nitrocatechol derivative of formula I is a mixture of two nitrocatechol derivatives, such as 2,5-dichloro-3-(5-(3,4-dihydroxy-5-nitrophenyl)-1,2,4-oxadiazol-3-yl)-4,6-dimethylpyridine 1-oxide and 5-[3-(2,5-dichloro-4,6-dimethylpyridin-3-yl)-[1,2,4]oxadiazol-5-yl]-3-nitrobenzene-1,2-diol, the ratio of the two components may be approximately 50:50 or any variation thereof, such as approximately 60:40, 70:30, 80:20, 90:10, 95:5, 97:3, or 99:1, or the proportion of one of the nitrocatechol derivatives may be present in an amount up to and including 5%, up to an including 3% or up to and including 1% of the amount of the other nitrocatechol, for example 5-[3-(2,5-dichloro-4,6-dimethylpyridin-3-yl)-[1,2,4]oxadiazol-5-yl]-3-nitrobenzene-1,2-diol may be present in an amount of up to and including 5%, up to and including 3% or up to and including 1% of the amount of 2,5-dichloro-3-(5-(3,4-dihydroxy-5-nitrophenyl)-1,2,4-oxadiazol-3-yl)-4,6-dimethylpyridine 1-oxide.

The at least one API chosen from nitrocatechol derivatives of formula I and salts, esters, hydrates, solvates and other derivatives thereof as disclosed herein may exhibit low bulk density, thereby making it difficult to formulate and manufacture a dosage form. For example, 2,5-dichloro-3-(5-(3,4-dihydroxy-5-nitrophenyl)-1,2,4-oxadiazol-3-yl)-4,6-dimethylpyridine 1-oxide may exhibit a bulk density of less than 0.1 g/ml prior to granulation and/or formulation, and 5-[3-(2,5-dichloro-4,6-dimethylpyridin-3-yl)-[1,2,4]oxadiazol-5-yl]-3-nitrobenzene-1,2-diol may exhibit a bulk density of around 0.2 g/ml prior to granulation and/or formulation, and as determined by the method described hereinbelow.

Formulating APIs of low bulk density can often give rise to many problems, for example poor content uniformity, particle segregation, little or no flowability, high average weight variability, capping and/or lamination of tablets, and high tablet friability.

In at least one exemplary embodiment, the amount (or dosage) of the at least one API present in the compositions and/or formulations of the present disclosure may be a therapeutically effective amount. As used herein, "therapeutically effective amount" means an amount of a therapeutic agent sufficient to treat, alleviate, and/or prevent any condition treatable and/or preventable by administration of a composition of the disclosure, in any degree. That amount can, for example, be an amount sufficient to exhibit a detectable therapeutic or preventative or ameliorative effect. The effect may include, for example, treatment, alleviation, and/or prevention of the conditions listed herein. The actual amount required, e.g. for treatment of any particular patient, will depend upon a variety of factors including the disorder being treated and/or prevented; its severity; the specific pharmaceutical composition employed; the age, body weight, general health, gender, and diet of the patient; the mode of administration; the time of administration; the route of administration; the rate of excretion of the therapeutic agent; the duration of the treatment; any drugs used in combination or coincidental with the therapeutic agent; and other such factors well known to those skilled in the art. In various embodiments, for example, a formulation, i.e, a capsule or tablet dosage form, may contain 1 mg or more of API, for example 2.5 mg or more, 5 mg or more, 10 mg or more, 20 mg or more, 40 mg or more, 50 mg or more, or 100 mg or more of API. The API content in the composition and/or formulation can therefore vary from 0.02 wt % to 90 wt % for example 0.1 wt % to 70 wt, 0.2 wt % to 50 wt % or 0.3 wt % to 45 wt %.

The at least one phosphate derivative of the present disclosure is any substance comprising calcium phosphate, including, but not limited to: calcium phosphate, dibasic anhydrous (for example, A-TAB™, Di-Cafos™, A-N, Emcompress™ Anhydrous, and Fujicalin™); calcium phosphate, dibasic dihydrate (for example, Cafos™, Calipharm™, Calstar™, Di-Cafos™, Emcompress™); and calcium phosphate tribasic (for example, Tri-Cafos™, TRI-CAL™ WG, TRI-TAB™).

In various embodiments, the amount of at least one phosphate derivative present in a composition and/or formulation of the present disclosure may constitute 0.5 wt % to 99.5 wt % of the composition and/or formulation, for example, 10 wt % to 80 wt %, 20 wt % to 60 wt %, or 25 wt % to 40 wt %, such as for example 35 wt %, of the total weight of the composition and/or formulation. The at least one phosphate derivative may be intragranular, extragranular, or part intragranular and part extragranular. The amount of the at least one phosphate derivative may vary depending, in part, upon the desired dosage and bulk density.

The at least one PVP derivative compound of the present disclosure is any substance comprising polyvinylpyrrolidone or a substituted version thereof, including, but not limited to: povidone (for example, Plasdone™ and Kollidon™); copovidone (for example, plasdone S-630™ and kollidon VA-64™); and cross-linked PVP (known also as crospovidone).

In various embodiments, the amount of at least one PVP derivative compound present in a composition and/or formulation of the present disclosure may constitute 0.1 wt % to 40 wt % of the composition and/or formulation, for example, 1 wt % to 30 wt %, 2 wt % to 20 wt %, 3 wt % to 10 wt %, or 6 wt % to 8 wt %, such as, for example 7 wt %, of the total weight of the composition and/or formulation. The PVP derivative compound may be intragranular, extragranular or part intragranular and part extragranular. The amount of the at least one PVP derivative compound may vary depending, in part, upon the desired dosage and bulk density.

The invention also relates to a method of making a composition or formulation of the inventions comprising the steps of:
granulating at least one active pharmaceutical ingredient chosen from nitrocatechol derivatives of formula I and salts, esters, hydrates, solvates and other derivatives thereof to form granules;
mixing at least one phosphate derivative with the at least one active pharmaceutical ingredient before, during or after granulation; and
mixing at least one polyvinylpyrrolidone derivative compound with the at least one active pharmaceutical ingredient before, during or after granulation.

In various exemplary embodiments of the present disclosure, the at least one API, at least one phosphate-derivative, and at least one PVP derivative compound are combined by mixing (also referred to herein as blending). The appropriate apparatus and mixing time and rate may be determined by those of skill in the art based on, for example, the amount of material present, the type of mixing process used, and other parameters known to those of skill in the art. For example, in various embodiments, the components may be mixed manually, using a V-blender, a high shear mixer, or any other mixing apparatus and/or process known to those of skill in the art. As a further example, in various embodiments, the components may be mixed for any appropriate period of time, such as 1 to 30 minutes or 2 to 10 minutes.

In various exemplary embodiments, granules may be formed by dry or wet granulation. In at least one embodiment, the granules are wet-granulated using at least one granulation liquid. By way of example, the at least one granulation liquid may be chosen from water, ethanol, isopropanol, and/or acetone. In at least one embodiment, the granulation liquid is water. The appropriate apparatus and mixing time and rate for granulation may be determined by those of skill in the art based on, for example, the amount of material and the amount of granulation liquid, if present. For example, in various embodiments, the components may be granulated manually, using a high shear mixer, planetary mixer or any other granulator apparatus and/or process known to those of skill in the art. As a further example, in various embodiments, the components may be granulated for any appropriate period of time, such as 1 to 60 minutes or 2 to 30 minutes. Determination of the endpoint of granulation is within the capability of the skilled person but can be determined by observance of stabilization of granule size and particle cohesion resulting in a decrease in air trapped inside the granule, or by attainment of steady state of rheological or correlated determination of voltage, conductivity torque, power consumption or near IR techniques. As a further example, granulation speeds may vary from 5 to 100% of the granulator mixing speed, such as from 25 to 100%.

In at least one exemplary embodiment, after the wet-granulation process is complete, the granules may then be dried. Granules should be dried to loss on drying (LOD) values below 6%, preferably below 5%, more preferably between 1-3%. A suitable technique for determining LOD values is as described in USP 31, vol. 1, test <731>, The United States Pharmacopeia Convention, 2008. The test involves accurately weighing the substance to be tested ($m_0$), (e.g. using a sample amount of 1 to 10 g). The test specimen is then dried at 105° C. until a constant weight ($m_f$) is achieved. The moisture can be calculated by using the following expression:

$$\text{LOD }(\%)=[(m_o-m_f)/m_0]*100$$

The appropriate drying apparatus and drying time and temperature may be determined by those of skill in the art based on, for example, the amount of material present, moisture content of the material, and the granulation liquid. As non-limiting examples, a fluid bed dryer or tray dryer may be used, for example at a temperature of 25° C. or higher, 40° C. or higher, or 70° C. or higher, to dry the granules. For example, the granules may be dried at a temperature of 66° C.

In various exemplary embodiments, the granules may be sieved. Sieving the granules may originate granules of homogeneous particle size, and may, for example, be used to select particles of an advantageous size for formulating or manufacturing a dosage form. In various embodiments, the granules may be sieved over a screen of 0.5 mm or larger, for example a 0.6 mm, 0.8 mm, 1.0 mm and 1.6 mm screen.

In various exemplary embodiments, the composition may include at least one excipient which may be blended with the at least one API, at least one phosphate derivative, and at least one PVP derivative compound. In one embodiment, the at least one excipient is blended with the API granules. The at least one excipient may be chosen from, but is not limited to, conventional excipients such as a) fillers, diluents or extenders, such as, for example, calcium carbonate, fructose or kaolin; b) binders such as, for example, acacia, sucrose and zein; c) disintegrants such as, for example, agar and calcium carbonate; d) lubricants such as, for example, calcium stearate, glycerine monostearate, glyceryl behenate, glyceryl palmitostearate, hydrogenated castor oil, hydrogenated vegetable oil type I, magnesium lauryl sulphate, magnesium stearate, medium-chain triglycerides, poloxamer, polyethylene glycol, sodium benzoate, sodium chloride, sodium lauryl sulphate, sodium stearyl fumarate, stearic acid, talc, sucrose stearate, and zinc stearate; and e) glidants such as, for example, tribasic calcium phosphate, calcium silicate, cellulose, powdered, colloidal silicon dioxide, magnesium silicate, magnesium trisilicate, starch, and talc. In further embodiments, the composition and/or formulation does not comprise any such additional excipients.

In various exemplary embodiments, the at least one excipient may be added before or during granulation of the at least one API and, thus, may be present as an intragranular excipient. In other exemplary embodiments, the at least one excipient may be added to the formulation after granulation, for example by blending with the granules, and thus may be present as an extragranular excipient. In various exemplary embodiments, at least one first excipient may be added prior to or during granulation and at least one second excipient and/or more of the at least one first excipient may be added to the composition after granulation. For example, in various embodiments, fillers, binders and disintegrants can be added prior to or during granulation, whereas flowability agents and glidants can be added after granulation.

In some exemplary embodiments, the composition and/or formulation comprise the following:

| | |
|---|---|
| API | 0.2-50.0 wt % |
| Phosphate derivate | 5.0-50.0 wt % |
| Additional Filler | 0.0-85.0 wt % |
| Povidone derivate | 1.0-15.0 wt % |
| Lubricants | 1.0-15.0 wt % |
| Disintegrants | 1.0-15.0 wt % |
| API | 0.2-30.0 wt % |
| Phosphate derivate | 20.0-50.0 wt % |
| Additional Filler | 0.0-85.0 wt % |
| Povidone derivate | 3.0-10.0 wt % |
| Lubricants | 1.0-10.0 wt % |
| Disintegrants | 3.0-10.0 wt % |
| API | 20.0-50.0 wt % |
| Phosphate derivate | 20.0-50.0 wt % |
| Additional Filler | 0.0-55.0 wt % |
| Povidone derivate | 3.0-10.0 wt % |
| Lubricants | 1.0-10.0 wt % |
| Disintegrants | 3.0-10.0 wt % |

In various exemplary embodiments, the composition comprising granules of the at least one API, the at least one phosphate derivative, and the at least one PVP derivative compound may be used to make a formulation, such as, for example, may be used to fill capsules or may be compressed to form tablets.

Capsules for use in the present disclosure include, but are not limited to, gelatin capsules and hydroxypropylmethyl cellulose (hypromellose) capsules. Suitable methods for filling such capsules with a composition according to an embodiment of the disclosure are well-known to those of skill in the art.

Tablets of the present disclosure may be formed by any method known to those of skill in the art such as compression. In at least one embodiment of the present disclosure, tablets may be coated, for example with aqueous based film-coatings, solvent based film-coatings and/or sugar coatings.

The formulations of the invention may also be colored, for example by inclusion of a coloring in the composition of the invention, or by coating the composition or formulation.

In various exemplary embodiments of the present disclosure, the compositions may exhibit improved bulk density and/or flow properties relative to those of the API alone. As used herein, the terms "improved bulk density," "significantly improved bulk density," and variations thereof mean that the bulk density of the composition is approximately at least double, at least three times, at least four times or at least five times that of the API alone. It is within the ability of one of skill in the art to determine the bulk density of a compound or composition using methods generally accepted in the art. However, suitable methods include, for example, the European Pharmacopeia edition 6, Test 2.9.15 "apparent volume," pages 285-286, EDQM, 2007, and USP 31, vol. 1 test <616> page 231-232, The United States Pharmacopeia Convention, 2008. An example of a suitable method is described below:

Apparatus:
settling apparatus capable of producing in 1 minute 250±15 taps from a height of 3±0.2 mm. The support for the graduated cylinder with its holder, has a mass of 450±5 g
a 250 ml graduated cylinder (2 ml intervals) with a mass of 220±40 g Method: Into a dry cylinder, introduce without compacting, 100.0 g (m g) of the test substance. Secure the cylinder in its holder. Read the unsettled apparent volume ($V_0$) to the nearest milliliter. Carry out 10, 500 and 1250 taps and read the corresponding volumes $V_{10}$, $V_{500}$, $V_{1250}$, to the nearest milliliter. If the difference between $V_{500}$ and $V_{1250}$ is greater than 2 ml, carry out another 1250 taps.

Alternatively, if it is not possible to select 100.0 g, select a test sample of any mass but with a volume between 50 ml and 250 ml, measure its apparent volume, $V_0$ as described above, and weigh the sample and specify the mass in the expression of results. Bulk/apparent density may then be determined in g/ml using the following formula:

$$m/V_0$$

where m is the mass in grams and $V_0$ the unsettled apparent volume.

Tapped apparent density may then be determined in g/ml using the following formula:

$$M/V_{1250}$$

where m is the mass in grams and $V_{1250}$ the apparent volume after 1250 hubs.

For example, as set forth above, 2,5-dichloro-3-(5-(3,4-dihydroxy-5-nitrophenyl)-1,2,4-oxadiazol-3-yl)-4,6-dimethylpyridine 1-oxide, a nitrocatechol of formula I, may exhibit a bulk density of less than 0.1 g/ml prior to granulating. Compositions according to the present disclosure comprising granules of 2,5-dichloro-3-(5-(3,4-dihydroxy-5- nitrophenyl)-1,2,4-oxadiazol-3-yl)-4,6-dimethylpyridine 1-oxide may exhibit bulk densities of 0.2 g/ml or greater, for example 0.4 g/ml or greater, or 0.5 g/ml or greater, or 0.6 g/ml or greater. In at least one embodiment of the disclosure, compositions of the present disclosure for use as final blends for capsule filling or tabletting comprising 2,5-dichloro-3-(5-(3,4-dihydroxy-5-nitrophenyl)-1,2,4-oxadiazol-3-yl)-4,6-dimethylpyridine 1-oxide may also exhibit bulk densities or apparent bulk densities of 0.2 g/ml or greater, for example 0.4 g/ml or greater, 0.5 g/ml or greater, or 0.6 g/ml or greater.

In at least one embodiment of the disclosure, compressed formulations of the disclosure such as tablets exhibit apparent density of 0.5 g/mL to 1.5 g/mL, such as 0.6 g/mL to 1.4 g/mL, 0.7 g/mL to 1.3 g/mL, or 0.8 g/mL to 1.2 g/mL.

The apparent density of a compressed formulation is measured in terms of mass and volume of the formulation and is well within the capabilities of the skilled person.

It is within the ability of one of skill in the art to determine the compressibility of a compound or composition using methods generally accepted in the art. However, suitable methods include but are not limited to, using USP 31, vol. 1, test <1174>, The United States Pharmacopeia Convention, 2008, and measuring both the bulk volume ($V_0$) and the tapped volume ($V_f$) of the granules. The compressibility index (CI) may then be calculated using the following formula:

$$CI\ (\%) = 100 \times [(V_0 - V_f)/V_0]$$

It is within the ability of one of skill in the art to determine the flowability of a compound or composition using methods generally accepted in the art. However, suitable methods include but are not limited to, testing the flow rate through an orifice described in USP 31, vol. 1, test <1174>, The United States Pharmacopeia Convention, 2008, in which case, the flowability may be measured as the mass per time flowing through the 10 mm diameter opening of a glass funnel.

Unless otherwise indicated, all numbers used in the specification and claims are to be understood as being modified in all instances by the term "about," whether or not so stated. It should also be understood that the precise numerical values used in the specification and claims form additional embodiments of the disclosure. Efforts have been made to ensure the accuracy of the numerical values disclosed in the Examples. Any measured numerical value, however, can inherently contain certain errors resulting from the standard deviation found in its respective measuring technique.

As used herein the use of "the," "a," or "an" means "at least one," and should not be limited to "only one" unless explicitly indicated to the contrary. Thus, for example, the use of "the formulation" or "a formulation" is intended to mean at least one formulation.

Other embodiments of the disclosure will be apparent to those skilled in the art from consideration of the specification and practice of the present disclosure. It is intended that the specification and examples be considered as exemplary only, with a true scope and spirit of the invention being indicated by the claims.

EXAMPLES

The following examples are not intended to be limiting of the invention as claimed.

Example 1

Four laboratory scale high dosage capsules were made by first mixing the API and dicalcium phosphate and/or microcrystalline cellulose, croscarmellose-sodium, and/or povidone, and/or pregelatinized starch in the amounts set forth in Table 1 below in a laboratory scale high shear mixer (Stephan). The API used in these examples was 2,5-dichloro-3-(5-(3,4-dihydroxy-5-nitrophenyl)-1,2,4-oxadiazol-3-yl)-4,6-dimethylpyridine 1-oxide. Purified water was added to each mixture, and the mixtures were granulated.

The granules were then dried in a laboratory scale fluid bed dryer (Aeromat). The dried granules were sieved and then blended with the remaining ingredients set forth in Table 1 in a 1 L tumble mixer (Turbula). Capsules were filled with the composition using a manual filling machine.

The granules and final compositions were evaluated for bulk and tapped density using the methods described above. Flowability was also accessed by testing the flow rate through an orifice described in USP 31, vol. 1, test <1174>, The United States Pharmacopeia Convention, 2008. The flowability was measured as the mass per time flowing through the 10 mm diameter opening of a glass funnel.

TABLE 1

| | Batch | | | |
| --- | --- | --- | --- | --- |
| Ingredient (%) | A | B | C | D |
| API | 35.1 | 35.1 | 35.1 | 35.1 |
| Di-Calcium-Phosphate | 33.3 | 33.3 | | |
| Microcrystalline Cellulose (Avicel PH 102) | 12.3 | 12.3 | 31.6 | |
| Microcrystalline Cellulose (Avicel PH 101) | | | | 45.6 |
| Croscarmellose-Sodium | 1.8 | | | |
| Povidone | 7.0 | | 7.0 | |
| Starch Pregelatinized | | 8.8 | | 8.8 |
| Purified Water | q.s. | q.s. | q.s. | q.s. |
| Microcrystalline Cellulose (Avicel PH 102) | | | 15.8 | |
| Croscarmellose-Sodium | 3.5 | 3.5 | 3.5 | 3.5 |
| Silica Colloidal Hydrate | 3.5 | 3.5 | 3.5 | 3.5 |
| Talc | 1.8 | 1.8 | 1.8 | 1.8 |
| Magnesium-Stearate | 1.8 | 1.8 | 1.8 | 1.8 |
| Bulk density granules [g/mL] | 0.425 | 0.365 | 0.323 | 0.236 |
| Tapped density of granules [g/mL] after | | | | |
| 10 hubs | 0.462 | 0.388 | 0.359 | 0.248 |
| 1250 hubs | 0.556 | 0.487 | 0.414 | 0.337 |
| Flowability granules | + + + | + + − | + + − | − − − |
| Bulk density final composition [g/mL] | 0.485 | 0.395 | 0.360 | 0.240 |
| Tapped density final composition [g/L] after | | | | |
| 10 hubs | 0.527 | 0.416 | 0.387 | 0.247 |
| 1250 hubs | 0.614 | 0.506 | 0.462 | 0.320 |
| Flowability final composition | + + + | + + − | + + − | + − − |

Flowability:
"+ + +" = very good;
"− − −" = not flowable

As can be seen from Table 1, although the presence of povidone or dicalcium phosphate improved bulk density and flowability properties (see Batches B and C) when compared to neither being present (see Batch D), the improvement in bulk density was significantly greater when both of these excipients were present (see Batch A). Similar flowability data were obtained for granules and final mixture, with the granules and final mixture of Batch A exhibiting very good flowability.

Example 2

To prepare low dosage capsules, two variations of the Batch A formulation were prepared at the laboratory scale.

The two batches of low dosage capsules were made using the compositions set forth in Table 2 below. First the API, dicalcium phosphate, microcrystalline cellulose, croscarmellose-sodium, and povidone in the amounts set forth in Table 3 below were mixed in a V-blender. The API used in these examples was 2,5-dichloro-3-(5-(3,4-dihydroxy-5-nitrophenyl)-1,2,4-oxadiazol-3-yl)-4,6-dimethylpyridine 1-oxide. Purified water was added to the mixture, and the mixture was mixed manually and granulated.

The granules were then dried in a tray dryer at 50° C. for about 300 minutes. The dried granules were sieved. The sieved granules were then blended with the remaining croscarmellose-sodium and silica colloidal hydrate set forth in Table 3 in a V-blender. Then the magnesium stearate and talc were added and mixed. Capsules were filled with the composition using a capsule filling machine.

The granules and final compositions were evaluated for bulk and tapped density and flowability using the methods described in Example 1 above. The compressibility index was assessed using USP 31, vol. 1, test <1174>, The United States Pharmacopeia Convention, 2008, and measuring both the bulk volume ($V_0$) and the tapped volume ($V_f$) of the granules. The compressibility index (CI) was then calculated using the following formula:

$$CI\ (\%) = 100 \times [(V_0 - V_f)/V_0]$$

The results are set forth in Table 2 below.

TABLE 2

| Ingredient (%) | Batch | |
| --- | --- | --- |
| | E | F |
| API | 1.8 | 1.8 |
| Di-Calcium-Phosphate, di-hydrated (Ecompress) | 33.3 | 57.9 |
| Microcrystalline Cellulose (Avicel PH 102) | 45.6 | 21.0 |
| Croscarmellose-Sodium | 1.8 | 1.8 |
| Povidone | 7.0 | 7.0 |
| Purified Water | q.s. | q.s. |
| Croscarmellose-Sodium | 3.5 | 3.5 |
| Silica Colloidal Hydrate | 3.5 | 3.5 |
| Talc | 1.8 | 1.8 |
| Magnesium-Stearate | 1.8 | 1.8 |
| Bulk density of granules [g/ml] | 0.53 | 0.63 |
| Tapped density of granules [g/ml] after 1250 hubs | 0.63 | 0.74 |
| Compressibility index (%) | 6.0 | 5.5 |
| Flow rate (g/sec) | 17.6 | 19.4 |

As seen in Table 2 above, the bulk density of the granules of Batch F was much higher than that of the high dosage formulations previously studied; therefore, it was not possible to fill capsules with granules from batch F with adequate mass. Batch E, however, gave rise to granules and capsules with similar properties to those of the high dosage formulations of Example 1. Batch E also presented good flow and compressibility properties.

Example 3

Three batches of pilot scale capsules of varying dosages were made using the compositions set forth in Table 3 below. Batch H is low dosage capsules, Batch J is intermediate dosage capsules, and Batch L is high dosage capsules.

First the API, dicalcium phosphate, microcrystalline cellulose, croscarmellose-sodium, and povidone in the amounts set forth in Table 3 below were mixed in a high-shear mixer granulator. The API used in these examples was 2,5-dichloro-3-(5-(3,4-dihydroxy-5-nitrophenyl)-1,2,4-oxadiazol-3-yl)-4,6-dimethylpyridine 1-oxide. Purified water was added to the mixture, and the mixture was mixed in a high-shear mixer granulator.

The granules were then dried in a fluid bed dryer. The dried granules were sieved. The sieved granules were then blended with the remaining croscarmellose-sodium and silica colloidal hydrate set forth in Table 3 in a V-blender. Then the magnesium stearate and talc were added and mixed. Capsules were filled with the compositions using a capsule filling machine.

Additionally, two laboratory scale batches were made, Batch G (low dosage) and K (high dosage), by the method set forth in Example 2. The compositions of these batches are set forth in Table 3 below.

The granules, compositions, and capsules were evaluated in the same manner set forth in Example 2, and the results are set forth in Table 3 below. Additionally, uniformity of mass was assessed by the individual weight of 20 capsules and average mass and standard deviation were calculated. These results are also set forth in Table 3.

TABLE 3

| Ingredient (%) | Batch | | | | |
| --- | --- | --- | --- | --- | --- |
| | G | H | J | K | L |
| API | 1.8 | 1.8 | 8.8 | 35.1 | 35.1 |
| Di-Calcium-Phosphate (Emcompress) | 33.3 | 33.3 | 33.3 | 33.3 | 33.3 |
| Microcrystalline Cellulose (Avicel PH 102) | 45.6 | 45.6 | 38.6 | 12.3 | 12.3 |
| Croscarmellose-Sodium | 1.8 | 1.8 | 1.8 | 1.8 | 1.8 |
| Povidone | 7.0 | 7.0 | 7.0 | 7.0 | 7.0 |
| Purified Water | q.s. | q.s. | q.s. | q.s. | q.s. |
| Croscarmellose-Sodium | 3.5 | 3.5 | 3.5 | 3.5 | 3.5 |
| Silica Colloidal Hydrate | 3.5 | 3.5 | 3.5 | 3.5 | 3.5 |
| Talc | 1.8 | 1.8 | 1.8 | 1.8 | 1.8 |
| Magnesium-Stearate | 1.8 | 1.8 | 1.8 | 1.8 | 1.8 |
| Bulk density of granules [g/ml] | 0.53 | 0.88 | 0.82 | 0.36 | 0.76 |
| Tapped density of granules [g/ml after 1250 hubs] | 0.63 | 0.91 | 0.87 | 0.43 | 0.83 |
| Compressibility index (%) | 6.0 | 5.4 | 6.7 | 10.5 | 6.2 |
| Flow rate (g/sec) | 17.6 | 23.5 | 24.6 | 18 | 23.4 |
| Uniformity mass (RSD %) of size 0 capsules | 4.2 | 2.4 | 2.6 | 5.3 | 2.9 |

The results set forth in Table 3 above show that most of the properties of the pilot scale batches were improved upon scale-up of the process (i.e., as compared to the batches set forth in Examples 1-2 above). Moreover, the bulk density, tapped density, and flow rate, in particular, indicate achievement of a final product with properties surprisingly superior to that of the API. The API used in the batches of the present example and the others set forth herein possesses a very low bulk density (<0.1 g/ml) and no flow; whereas, the granules of some of the present batches exhibit bulk densities higher than 0.8 g/ml (an increase of over 800%) and a flow rate higher than 20 g/s. Even at high API doses (e.g., around 35%) the bulk density was greatly improved: from less than 0.1 g/ml to 0.76 g/ml.

Comparative Example 1

Five high dosage capsules were made by first mixing the API, the first microcrystalline cellulose amount, the first ethylcellulose amount and the maize starch in the amounts set forth in Table 4 in a high shear mixer. The API used in these examples was 2,5-dichloro-3-(5-(3,4-dihydroxy-5-nitrophenyl)-1,2,4-oxadiazol-3-yl)-4,6-dimethylpyridine 1-oxide. Purified water was added to each mixture, and the mixtures were granulated.

The granules were then dried in a fluid bed dryer (Aeromat). The dried granules were sieved and then blended with the remaining ingredients set forth in Table 4 in a 1 L tumble mixer (Turbula). Capsules were filled with the composition using a manual filling machine.

TABLE 4

| Ingredient (%) | Batch: | | | | |
| --- | --- | --- | --- | --- | --- |
|  | CA | CB | CC | CD | CE |
| API | 35.1 | 35.1 | 35.1 | 35.1 | 35.1 |
| Microcrystalline Cellulose | 17.5 |  | 17.5 |  | 15.8 |
| Ethylcellulose |  | 1.8 |  | 1.8 | 1.8 |
| Maize Starch | 8.8 | 8.8 | 8.8 | 8.8 | 8.8 |
| Purified Water | q.s. | q.s | q.s | q.s. | q.s. |
| Microcrystalline Cellulose | 28.1 | 43.9 |  |  | 14.0 |
| Ethylcellulose |  |  | 28.1 | 43.9 | 14.0 |
| Croscarmellose-Sodium | 3.5 | 3.5 | 3.5 | 3.5 | 3.5 |
| Silica Colloidal Hydrate | 3.5 | 3.5 | 3.5 | 3.5 | 3.5 |
| Talc | 1.8 | 1.8 | 1.8 | 1.8 | 1.8 |
| Magnesium-Stearate | 1.8 | 1.8 | 1.8 | 1.8 | 1.8 |
| Bulk density of granules [g/mL] | 0.175 | 0.120 | 0.150 | 0.100 | 0.114 |
| tapped density granules [g/mL] after | | | | | |
| 10 hubs | 0.177 | 0.124 | 0.156 | 0.103 | 0.118 |
| 1250 hubs | 0.278 | 0.190 | 0.246 | 0.172 | 0.190 |
| flowability granules | - - - | - - - | - - - | - - - | - - - |
| bulk density final mixture [g/mL] | 0.210 | 0.210 | 0.195 | 0.190 | 0.185 |
| tapped density final mixture [g/mL] after | | | | | |
| 10 hubs | 0.217 | 0.217 | 0.203 | 0.200 | 0.197 |
| 1250 hubs | 0.292 | 0.292 | 0.275 | 0.271 | 0.253 |
| flowability final mixture | + - - | + - - | + - - | + - - | + - - |

The granules and final compositions were evaluated in the manner set forth in Example 1 and the results are set forth in Table 4 above. The formulations exhibited little to slight improvement in bulk density and poor to insufficient flowability properties.

What is claimed is:

1. A method of treating Parkinson's disease, parkinsonian disorders, or restless leg syndrome, said method comprising administering a composition comprising granules comprising 2,5-dichloro-3-(5-(3,4-dihydroxy-5-nitrophenyl)-1,2,4-oxadiazol-3-yl)-4,6-dimethylpyridine 1-oxide to a patient, wherein the composition has a bulk density greater than 0.2 g/mL.

2. The method according to claim 1, wherein the disorder is chosen from Parkinson's disease.

3. The method according to claim 1, wherein the composition further comprises 5-[3-(2,5-dichloro-4,6-dimethylpyridin-3-yl)-[1,2,4]oxadiazol-5-yl]-3-nitrobenzene-1,2-diol.

4. The method according to claim 3, wherein the ratio of the 2,5-dichloro-3-(5-(3,4-dihydroxy-5-nitrophenyl)-1,2,4-oxadiazol-3-yl)-4,6-dimethylpyridine 1-oxide to the 5-[3-(2,5-dichloro-4,6-dimethylpyridin-3-yl)-[1,2,4]oxadiazol-5-yl]-3-nitrobenzene-1,2-diol ranges from about 99:1 to about 95:5.

5. The method according to claim 3, wherein the 5-[3-(2,5-dichloro-4,6-dimethylpyridin-3-yl)-[1,2,4]oxadiazol-5-yl]-3-nitrobenzene-1,2-diol is present in an amount up to about 5% by weight, relative to the 2,5-dichloro-3-(5-(3,4-dihydroxy-5-nitrophenyl)-1,2,4-oxadiazol-3-yl)-4,6-dimethylpyridine 1-oxide.

6. The method according to claim 3, further comprising at least one additional component chosen from fillers, diluents, binders, disintegrants, lubricants, and glidants.

7. The method according to claim 3, wherein the bulk density of the composition is greater than 0.3 g/mL.

8. A method of treating Parkinson's disease, parkinsonian disorders, or restless leg syndrome, the method comprising administering a pharmaceutical formulation comprising a composition comprising granules comprising 2,5-dichloro-3-(5-(3,4-dihydroxy-5-nitrophenyl)-1,2,4-oxadiazol-3-yl)-4,6-dimethylpyridine 1-oxide to a patient, wherein the composition has a bulk density greater than 0.2 g/mL.

9. The method according to claim 8, wherein the disorder is chosen from Parkinson's disease.

10. The method according to claim 8, wherein the formulation is a dosage form chosen from tablets and capsules.

11. The method according to claim 8, wherein the formulation is a capsule.

12. The method according to claim 8, wherein the total amount of the 2,5-dichloro-3-(5-(3,4-dihydroxy-5-nitrophenyl)-1,2,4-oxadiazol-3-yl)-4,6-dimethylpyridine 1-oxide is at least 10 mg.

13. The method according to claim 8, wherein the composition further comprises 5-[3-(2,5-dichloro-4,6-dimethylpyridin-3-yl)-[1,2,4]oxadiazol-5-yl]-3-nitrobenzene-1,2-diol.

14. The method according to claim 13, wherein the formulation is a dosage form chosen from tablets and capsules.

15. The method according to claim 13, wherein the formulation is a capsule.

16. The method according to claim 13, wherein the total amount of the 2,5-dichloro-3-(5-(3,4-dihydroxy-5-nitrophenyl)-1,2,4-oxadiazol-3-yl)-4,6-dimethylpyridine 1-oxide and the 5-[3-(2,5-dichloro-4,6-dimethylpyridin-3-yl)-[1,2,4]oxadiazol-5-yl]-3-nitrobenzene-1,2-diol is at least 10 mg.

17. The method according to claim 8, wherein the total amount of the 2,5-dichloro-3-(5-(3,4-dihydroxy-5-nitrophenyl)-1,2,4-oxadiazol-3-yl)-4,6-dimethylpyridine 1-oxide is at least 20 mg.

18. The method according to claim 8, wherein the total amount of the 2,5-dichloro-3-(5-(3,4-dihydroxy-5-nitrophenyl)-1,2,4-oxadiazol-3-yl)-4,6-dimethylpyridine 1-oxide is at least 50 mg.

19. The method according to claim 8, wherein the total amount of the 2,5-dichloro-3-(5-(3,4-dihydroxy-5-nitrophenyl)-1,2,4-oxadiazol-3-yl)-4,6-dimethylpyridine 1-oxide is about 25 mg.

20. The method according to claim 8, wherein the total amount of the 2,5-dichloro-3-(5-(3,4-dihydroxy-5-nitrophenyl)-1,2,4-oxadiazol-3-yl)-4,6-dimethylpyridine 1-oxide is about 50 mg.

21. The method according to claim 13, wherein the total amount of the 2,5-dichloro-3-(5-(3,4-dihydroxy-5-nitrophenyl)-1,2,4-oxadiazol-3-yl)-4,6-dimethylpyridine 1-oxide and the 5-[3-(2,5-dichloro-4,6-dimethylpyridin-3-yl)-[1,2,4]oxadiazol-5-yl]-3-nitrobenzene-1,2-diol is at least 20 mg.

22. The method according to claim 13, wherein the total amount of the 2,5-dichloro-3-(5-(3,4-dihydroxy-5-nitrophenyl)-1,2,4-oxadiazol-3-yl)-4,6-dimethylpyridine 1-oxide and the 5-[3-(2,5-dichloro-4,6-dimethylpyridin-3-yl)-[1,2,4]oxadiazol-5-yl]-3-nitrobenzene-1,2-diol is at least 50 mg.

23. The method according to claim 13, wherein the total amount of the 2,5-dichloro-3-(5-(3,4-dihydroxy-5-nitrophenyl)-1,2,4-oxadiazol-3-yl)-4,6-dimethylpyridine 1-oxide and the 5-[3-(2,5-dichloro-4,6-dimethylpyridin-3-yl)-[1,2,4]oxadiazol-5-yl]-3-nitrobenzene-1,2-diol is about 25 mg.

24. The method according to claim 13, wherein the total amount of the 2,5-dichloro-3-(5-(3,4-dihydroxy-5-nitrophenyl)-1,2,4-oxadiazol-3-yl)-4,6-dimethylpyridine 1-oxide and the 5-[3-(2,5-dichloro-4,6-dimethylpyridin-3-yl)-[1,2,4]oxadiazol-5-yl]-3-nitrobenzene-1,2-diol is about 50 mg.

* * * * *